(12) United States Patent
Hjertman et al.

(10) Patent No.: US 7,396,347 B2
(45) Date of Patent: *Jul. 8, 2008

(54) INJECTOR DEVICE AND METHOD FOR ITS OPERATION

(75) Inventors: Birger Hjertman, Vällingby (SE); Rudolf Cseke, Sollentuna (SE)

(73) Assignee: Pfizer Health AB, Stockholm (SE)

( * ) Notice: Subject to any disclaimer, the term of this patent is extended or adjusted under 35 U.S.C. 154(b) by 737 days.

This patent is subject to a terminal disclaimer.

(21) Appl. No.: 10/397,133

(22) Filed: Mar. 26, 2003

(65) Prior Publication Data
US 2003/0158523 A1    Aug. 21, 2003

Related U.S. Application Data

(63) Continuation of application No. 09/549,373, filed on Apr. 14, 2000, now Pat. No. 6,562,006.

(30) Foreign Application Priority Data
Apr. 16, 1999    (SE) .................................... 9901366

(51) Int. Cl.
*A61M 5/00*    (2006.01)
(52) U.S. Cl. .................................... 604/207
(58) Field of Classification Search .............. 604/207, 604/208, 209, 210, 211, 218, 181, 184, 186, 604/187
See application file for complete search history.

(56) References Cited

U.S. PATENT DOCUMENTS

| | | | |
|---|---|---|---|
| 3,517,668 A | | 6/1970 | Brickson |
| 4,050,459 A | * | 9/1977 | Sanchez ..................... 604/210 |
| 4,475,905 A | | 10/1984 | Himmelstrup |
| 4,610,668 A | * | 9/1986 | Fleig .......................... 604/208 |
| 4,832,694 A | | 5/1989 | Raphael, III et al. |
| 4,874,381 A | | 10/1989 | Vetter |

(Continued)

FOREIGN PATENT DOCUMENTS

DE    8509572    9/1985

(Continued)

OTHER PUBLICATIONS

McPhee et al, *Current Medical Diagnosis & Treatment 2001*, Lange Medical Books/McGraw-Hill, 40th Ed., p. 24.

*Primary Examiner*—Nicholas D. Lucchesi
*Assistant Examiner*—Theodore J Stigell
(74) *Attorney, Agent, or Firm*—Dinsmore & Shohl LLP

(57) ABSTRACT

Injector device, and method for its operation, for containers of syringe type, comprising a barrel of axially roughly constant cross-section, a front opening and at least one movable wall inserted in the barrel for displacement of a container content, the injector comprising a) a housing or housing part arranged to receive the container at least axially stationary, b) an integral or composite piston rod arrangement operable to displace the container movable wall at least in the forward direction and c) a track system for controlling or sequencing the piston rod movements, the track system comprising at least one cooperating track and follower, the cooperating track and follower being arranged stationary with respect to the housing and the piston rod respectively, or vice versa, and in cooperation allowing at least one forward for the piston rod. The track system comprises arrangements initiation, dose setting and expulsion of container content.

33 Claims, 3 Drawing Sheets

U.S. PATENT DOCUMENTS

| | | | |
|---|---|---|---|
| 4,936,833 A | 6/1990 | Sams | |
| 4,968,299 A | 11/1990 | Ahlstrand et al. | |
| 5,080,649 A | 1/1992 | Vetter | |
| 5,092,824 A | 3/1992 | Connett | |
| 5,092,842 A | 3/1992 | Bechtold et al. | |
| 5,244,465 A | 9/1993 | Michel | |
| 5,318,544 A | 6/1994 | Drypen et al. | |
| 5,454,793 A | 10/1995 | Levander et al. | |
| 5,582,598 A * | 12/1996 | Chanoch | 604/208 |
| 5,634,910 A * | 6/1997 | Kanner et al. | 604/208 |
| 5,645,926 A | 7/1997 | Horrocks et al. | |
| 5,728,075 A | 3/1998 | Levander | |
| 5,807,346 A | 9/1998 | Frezza | |
| 5,836,359 A * | 11/1998 | Seidler | 141/23 |
| 5,950,690 A * | 9/1999 | Seidler | 141/23 |
| 6,083,201 A * | 7/2000 | Skinkle | 604/151 |
| 6,277,101 B1 | 8/2001 | Kirchhofer et al. | |
| 6,348,043 B1 * | 2/2002 | Hagen et al. | 604/151 |
| 6,562,006 B1 * | 5/2003 | Hjertman et al. | 604/208 |

FOREIGN PATENT DOCUMENTS

| | | |
|---|---|---|
| EP | 0956874 | 11/1999 |
| GB | 1230522 | 5/1968 |
| TW | 336897 | 7/1998 |
| WO | WO9736625 | 10/1997 |

* cited by examiner

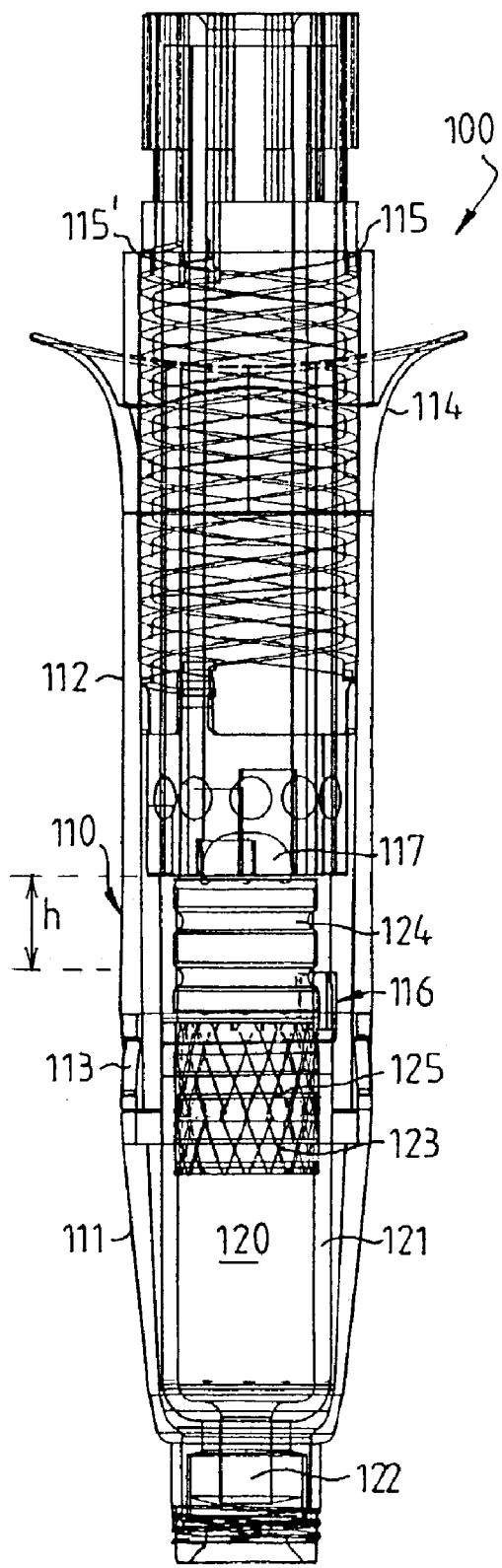
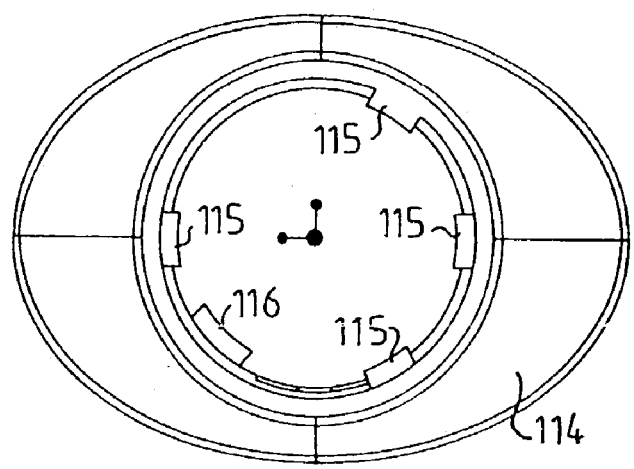
FIG. 1A
FIG. 1B

INJECTOR DEVICE AND METHOD FOR ITS OPERATION

RELATED APPLICATION

The present application is a continuation of prior application Ser. No. 09/549,373 filed Apr. 14, 2000, now U.S. Pat. No. 6,562,006 B1.

TECHNICAL FIELD

The present invention relates to an injector device for containers of syringe type, comprising a barrel of axially roughly constant cross-section, a front opening and at least one movable wall inserted in the barrel for displacement of a container content, the injector comprising a) a housing or housing part arranged to receive the container at least axially stationary, b) an integral or composite piston rod arrangement operable to displace the container movable wall at least in the forward direction and c) a track system for controlling or sequencing the piston-rod movements the,track system comprising at least one cooperating track and follower, the cooperating track and follower being arranged stationary with respect to the housing and the piston rod respectively, or vice versa, and in cooperation allowing at least one forward for the piston rod. The invention also relates to a method for operating such a device.

BACKGROUND

Although simple in principle injection procedures based on syringe type devices with injection needles require mastering of several discrete steps. Before the mere injection procedure some initiation actions may be required. Filling the syringe with medication withdrawn from a reservoir such as a vial may be needed, taking into account the proper dose to be administered. In order to avoid this step in the actual treatment situation it is common to provide pre-filled syringes, in which case, however, a dose setting or selecting step may be needed. In its first movement the syringe piston may need an extraordinary break-loose force after storage to overcome both internal reshaping resistance and an increased wall friction due to adherence or depletion of lubricant in contact points. For storage and shelf life reasons pre-filled syringes sometimes are delivered in dual or multiple-chamber form, requiring an additional mixing step immediately before treatment. De-aeration and pre-ejection are generally needed to remove gas in the vessel compartment and fill out spaces for example at the front sealing, outlet attachments and the interior of the outlet devices or needles. Syringes containing multiple doses further requires repeated ejection of predetermined volumes under avoidance of both over and under dosing, overdosing generally being irreversible and under-dosing often being undetected or unavoidable when ejecting an insufficient last dose from the syringe. Proper sequencing of all these steps are crucial to a safe and non-traumatic treatment.

These demands can be met also when using the simplest injection devices, such as the common hypodermic syringe, when in the hands of a skilled operator who also may initiate medically relevant corrective measures in case of accidents and malfunction. However, a general treatment trend is to place administration responsibility on the patients themselves, also in the case of child, elderly and disabled persons. In long-term treatment the patient often develop a certain skill but less frequent administration schemes also exist, often including situations of emergency or patient imbalance. Other unique problems in patient selfadministration, as compared to assistant operated administration, is that less suitable and often strained body positions are required and that apprehended or experienced pain or discomfort may interfere with the medically desirable action pattern. In summary, especially the selfadministration requires more sophisticated devices to facilitate the injection procedure and avoid or reduce risks for mistakes. Patients dependent on daily or occasional administrations also have a legitimate need for convenience and devices discrete enough to be brought around in daily life. Yet it is desirable that such sophistication and convenience is kept simple and inexpensive to allow for widespread distribution and inclusion also in disposable devices.

Various proposals have been put forward for injector devices assisting the user in many of the steps outlined. While meritorious in some respects none seem to deal with more than part of the total sequence. The U.S. Pat. No. 5,244,465 patent specification describes limiting arrangements for securing a single ejection of one of several selectable dose volumes. The U.S. Pat. No. 4,050,459, GB 1230522 and DE G8509572 specifications describe various trail for securing repeated multiple equal doses of predetermined volume. The U.S. Pat. Nos. 3,517,668 and 5,807,346 patent specifications and the PCT/CH96/00115 application describe arrangements for multiple ejections of selectable dose volumes. The U.S. Pat. No. 4,832,694 specification describes a trail arrangement for a single aspiration and ejection cycle under prevention of any reverse movement. The specifications referred to do not give any solutions to the earlier phases in injection sequence or how to integrate such phases. The U.S. Pat. Nos. specifications 4,968,299, 4,874,381, 5,080,649 and 5,728,075 and WO 93/14799 all relates to arrangements for securing mixing of contents in two chamber syringes followed by injection, utilizing a screw-threaded mechanism for the mixing phase. Again these suggestions only relate to a part of the overall operation.

Accordingly there is a continuing need for simple and inexpensive injection devices able to assist the user in the various handling steps involved, preventing or ameliorating mistakes and offering an ergonomic, convenient and non-traumatic product, especially useful for patients under self-administration. Although the present invention may have a more general utility, it will mainly be described against this background.

SUMMARY OF INVENTION

A main object of the present invention is to avoid the disadvantages of known injection devices as described. A more specific object is to provide an injection device able to assist the user in proper performance of all or most operation steps up to and including injection, such as, when applicable, chamber mixing, de-aeration, dose selection and ejection of single or repeated pre-determined doses. Another object is to provide a device assisting the user in securing a proper sequencing of such steps. Still another object is to provide a device being mechanically programmed for proper sequencing. A further object is to provide a device with improved dose setting properties and suitable for delivery of varying doses. Yet another object is to provide a device usable for single or multiple controlled ejections from a container. Another other object is to provide a device compatible with pre-filled syringes of various natures. Still another object is to provide a device suitable for self-administration. A further object is to provide a device convenient to handle. Yet another object is to provide a device having few and simple parts, yet giving high operation safety and precision. Still another object is to provide a device easy to manufacture and assemble. Another object is to provide a simple device of low cost, usable as a disposable device. A further object is to provide methods for operating the devices as described.

These objects are reached with the device and method having the characteristics set forth in the appended claims.

By use of a program arrangement based on a system of cooperating tracks and track followers several objects are met. An overall simple design is possible, which can be implemented in low cost parts. It also allows high flexibility in part selection for the cooperating parts and few components are needed if placed on the standard syringe parts, such as housing and piston rod construction, and even so a track can be arranged either on one or the either part, with the follower on the opposite, or a combination thereof for highest program flexibility and for allowing secondary considerations, e.g. in respect of strength and manufacture. The system can be used to positively urge the user into one action sequence only and can even be made irreversible by use of one-way structures. Yet the system is also compatible with reversible action at selected points in the sequence, e.g. when setting the dose, by simply allowing two-directional relative track and follower movements or such movement in an endless loop, e.g. around the device circumference. It is compatible with both axial and rotational movements, and combinations thereof, and can serve to give force or speed transformation, such as in a screw-threaded track, e.g. high force for piston break-loose and low speed for cautious mixing. Use of several track parts branching off from a common track part makes it possible to select one of several programmed paths, e.g. for setting variable doses. Guided multiple dosing systems are offered, e.g. by extending track parts into consecutive axial and transversal parts, optionally with repeated branching to create multiplied alternatives. This with maintained option of combining with a common program part, e.g. for initiation steps with compulsory change therebetween, including de-aeration and unification movements for multiple chamber containers, the latter with option of combining with screw-threaded track parts, as known per se. The system can be divided into more than one track and follower parts, if arranged so that the parts do not counteract, for further program flexibility or design freedom, e.g. with consideration to device size, strength, manufacture etc., or to allow for different characteristics in the various program phases, e.g. several followers for mechanical rigidity in phases not requiring many alternatives, such as initiation, whereas a single follower can be used for phases requiring several alternatives, notably dose setting, for full utilization of available surface for program structures or indicia. It should be noted that in spite of the multitude of functions possible the device can be extremely simple and in its most extreme form the entire track system can be molded or pressed into one surface, e.g. the piston rod outer surface or the hosing inner surface with the follower point structures on the opposing surface, requiring no more than minimum parts. This in strong contrast to prior art devices, which typically require multiple parts already for dose setting, offers multiple ejections only of one dose or requires additional reciprocating parts, use different mechanisms for multiple chamber mixing and often neglect or and leaves to the user the problem of de-aeration and pre-ejection. The simplicity provided meets the objects of device low cost, small size and suitability for disposable design. It also meets the objects of easy manufacture, assembly and compatibility with various container designs. The complete programming and few movements required meet the objects of safety, convenience and suitability for use in patient self-administration.

Further objects and advantages will be evident from the detailed description of the invention hereinbelow.

DETAILED DESCRIPTION

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description actions.

The injector described herein may be used for a variety of purposes within and beyond the medical area and for any type of preparations, such as chemicals, compositions or mixtures, in any container and delivered for any purpose. For reasons outlined the system have certain special values in connection with medical delivery devices where also the design constraints are more severe than in most other applications. For convenience the invention will be described in terms of this application.

Normally the material to be delivered is a fluid and preferably a liquid, including materials behaving as liquids such as emulsions or suspensions. These observations relate to the final preparation whereas other components, notably solids, may be present before final preparation. The nature of container content shall also be understood to include medical in broad terms and to embrace for example natural components and body fluids pre-filled or drawn into the container although most commonly the medical is factory prepared. Although the principles of the invention are mainly described with respect to ejection they are equally applicable for aspiration steps.

The containers usable in the present injectors generally comprises a container for the preparation and an opening through which the preparation can be delivered and a broad range of container types are useful. Syringe type containers are preferred for use in the present injector and shall be understood in broad terms and can generally be said to include a barrel having a front part and a rear part defining a general axis, an outlet for the preparation, typically comprising a liquid in broad sense, arranged at the front part and at least one movable wall arranged at the rear part, a displacement of which wall causes the preparation to be moved towards or expelled through the outlet. Barrel shape and movable wall have to be mutually adapted. The barrel of for example glass or plastic may have a substantially constant internal cross-section, with a similarly constant barrel axis, between front and rear parts giving generally tube-shaped barrel, and most preferably the cross-section is of the common circular type giving a substantially cylindrical barrel. The movable wall is then preferably a substantially shape-permanent, although possibly elastic, body sealingly adapted to the internal barrel surface and preferably of the piston type. Depending on the use purpose for the injector, at the outlet a needle, a cannula, an infusion tube or a similar delivery may be in fluid connection with the opening, e.g. by being arranged on, at or with a conduit to the opening. Within these limits and preferences a broad range of syringe type containers can be used with the present injector device, such as ampoules, cartridges, carpoules and syringes. It is also within the spirit of the invention that the container is not a separate part from the housing but that the housing integrally comprises the container although in most instances it is preferred that the container is a separate part. The container need not have a separate plunger but it is preferred that the piston rod to be described can act more or less directly on the container movable wall, although it is fully possible that the container has a plunger, in the sense of a part protruding from barrel rear end, on which the injector piston rod can act for movement of the piston, since many standardized devices are so designed. The injector can with preference be used with standard container types, e.g. as defined in DIN and ISO standards. Also usable are dual or multi chamber container types, known e.g. for preparations demanding a mixing of two or more components or precursors before administration. The components are kept separated by one or more intermediate walls of different known designs, which walls divide the barrel into several chambers, sometimes placed parallel along cartridge axis but most commonly in stacked relationship along the axis. Unification of the components may take place by breaking, penetrating or opening a valve construction in the intermediate walls. In another known design the intermediate wall or walls are of the piston type and flow communication between the chambers is accomplished by moving the piston to a by-pass section where the interior wall has one or several enlarged sections or repeated circumferential grooves and lands or piston deforming structures in a manner allowing by-flow of rear chamber content into front chamber at displacement of the rear movable wall. For the present purposes it is preferred to use multiple chamber designs where mixing can be achieved by an axial movement of the piston rod, either a straight axial movement or a screw movement as known per se. The chambers may contain gas, liquid or solids. Generally at least one liquid is present. Most commonly in pharmaceutical applications only two chambers are present and typically contains one liquid and one solid, the latter being dissolved and reconstituted during the mixing operation. For these types of containers it is possible both that the mixing or reconstitution step has already taken place when the container is placed in the injector or that means are provided within the device for unifying the chamber contents before the actual injection process is started.

As used herein positional and directional statements shall be understood with reference to the container. The "axis" or "axial" direction refers to the axis along which the container barrel has substantially constant cross-section. The "front" refers to the barrel end having the opening for content flow and "forward" to directions from the barrel side towards the opening and "rear" and "rearwards" to the opposite end and direction. "Transversal" refers to a direction perpendicular to the axial direction and includes "rotational" movements around a line parallel or concentric with the axis. Unless otherwise indicated use of the directional statements, such as "axial" or "rotational" shall not be understood to be restricted to purely the indicated direction but shall be understood to incorporate everything having a component in the indicated direction.

The injector device comprises a housing, which shall be understood in broad sense as long as it performs its basic functions of supporting the container and having, or providing support for, the track or follower structures to be described. The container may be movably arranged with respect to the housing, e.g. to allow initiation steps under movement relative the housing such as under mixing of mixing of multiple chamber containers as known per se, although for the present purposes it is preferred to perform even such steps with the container stationary with respect to the housing. Unless otherwise indicated the container shall be assumed to be stationary, at least in the axial direction, with respect to the housing. The container can be attached to the housing in such a manner that it remains exposed, although it is preferred that the housing also confines the container. The housing should leave exposed parts operated by the user, notably the piston rod when manually operated and for example needle attachments. As indicated it is often preferred to use the device as a disposable in which case it is preferred to factory load it with the container and a simple closure arrangement is of value for rational assembly in manufacture. In broad terms the housing shape is not critical for the basic function of the device but may influence its ergonomic and convenience properties and as common in the art the housing may have a design facilitating it manipulation, such as fingergrips and other grip surfaces. Otherwise the overall shape of the housing can take a variety of shapes depending on among others the internal component layout. The housing may be a single or multiple piece part although it is preferred to design it with as few parts as possible. Preferably housing parts are made from plastic material by for example moulding.

The injector comprises a piston rod, which shall also be understood in a broad sense as long as it performs its basic functions of being able to displace the movable wall and having, or providing support for, the track or follower structures to be described. The piston rod need to be movably arranged in relation to the container and is preferably also movably arranged with respect to the housing. It should at least be movable in the axial direction but in order to increase the program design freedom it is preferably also movable in the transversal direction, preferably by being rotatable, preferably around the container axis. Generally the piston rod comprises a penetrating part designed to penetrate into the container barrel and preferably also have an accessible part remaining outside, e.g. providing access for manipulation. The piston rod can be moved by an actuator system incorporating stored energy, e.g. by springs, compressed or generated gas or electric motor means, but when simplicity is important it is preferred to design the piston rod for manual actuation for which the principles of the invention are also well suited. The track and follower structures can be arranged on different parts of the piston rod, a track even on the penetrating part whereas a follower preferably is arranged on an accessible part. When essential parts of the track are arranged on the piston rod it has been found beneficial to provide for a large surface on the piston rod, e.g. by making the penetrating part as large as the barrel size allows. A preferred way to increase the available surface is to enlarge the accessible part of the piston rod, which part in principle can be made as large as required in length and width, which has the additional advantage of allowing small containers, and to locate track parts to these enlarged surfaces of the piston rod. The enlarged surface can be arranged axially rearwards of the penetrating part but it is preferred that it extends axially forwards to at least partially extend over the container barrel outside when the penetrating part moves into the barrel. Preferably the penetrating part and the extended part run at least partly in parallel to accommodate the barrel therebetween. Most preferably the extended part of the accessible part has the overall shape of a tube or sleeve concentric with the penetrating part. The general layout described gives manufacturing and rigidity advantages in addition to the track structure benefits. Also the piston rod can be designed as a multipart piece although it is preferred an possible to make it as a single piece. Preferably the piston rod is molded in plastic.

Tracks can be provided on either a housing part, a piston rod part or on both. The followers shall be arranged on the opposite housing or piston rod part, having the track with which it arranged to cooperate. For purpose of track system description, any other injector part, such as an intermediate part, shall be regarded as part of the housing or the piston rod respectively depending on its functional relationship thereto, mainly with which part it moves Tracks can be arranged on the housing, for example on the housing interior surface or as slits in the housing wall, with one or more followers on the piston rod, which for example allows for a slim device. It is preferred to place tracks on the piston rod with one or more followers on the housing part, which among others allows for rigidity, ease of manufacture and flexibility in track layout. It is possible to place tracks on both the housing and the piston rod although it is generally more advantageous to have tracks only on one of the parts.

The physical implementation of the tracks can take a variety of forms. The track may be a raised rail gripped by a correspondingly shaped follower. Especially in thin materials the track may be a slit. Tracks in the form of grooves are generally preferred among others for rigidity and ease of manufacture. Such a groove may have cross-section for example being concave, rectangular or with undercut, e.g. for catching a correspondingly shaped follower. The tracks in general preferably having constant cross-section over a certain extension corresponding to at least several times their width and may be so in their entire length but it is also possible that the cross-section changes, for example at a knee or bend, e.g. to accommodate an asymmetrical follower, which may be used to meet different space or strength limitations in different directions. Mostly it is preferred that the track guides the follower line movement only, which need not and most often is not straight, so that movements away from the line are prevented. The track may, however, also widen or disappear at certain locations, e.g. to release a follower for example when another follower is engaged, to allow several movements or where a guided movement is not necessary. In such situations the line guidance of the follower can be said to widen into an area. Another similar situation is when it is only necessary or suitable to guide the follower movement against dislocations towards one of the lateral sides of the track, e.g. when dislocations to the other side is prevented by other means for example a second track or follower, when a pumping action is allowed or to allow entrance of a follower into the track from more than one or numerous positions. The track may then be reduced to a one-sided track, e.g. an edge.

Also the followers can take a variety of shapes. The follower can basically be regarded as a "point" structure able to pass along the line or area provided by the track and should have physical dimensions slightly less than the track parts to be passed, except where friction controlled elements are arranged to be described. It can with preference be symmetrical, e.g. have a round or square cross-section when seen perpendicular to the track plane. The follower may, however, also be asymmetrical, e.g. longer than wide, when only unidirectional movements are needed or even in multi-directional tracks if the track changes cross-section when it changes direction to accommodate the new width of the follower or if the follower is movably, e.g. rotationally attached to its substrate, which also can be used to allow adaptation to threads of varying pitch. The follower cross-section when seen along the track may be adapted to the corresponding track cross-section although it is not necessary and sometimes a non-congruent shape is preferred, e.g. giving point rather than surface contact between track and follower for reduced friction. The follower may also be movable in a direction substantially perpendicular to the track carrying surface, e.g. to allow engagement or disengagement with the track, preferably biased in one direction by spring or material resilience, for automatic or manually assisted control. In the later case, the follower is preferably arranged on the housing.

Any track can have additional control elements as known per se, such as one-way structures, facilitating follower movement in one direction in the track but preventing movement in the opposite direction, e.g. in the form of a hinged stop surface yielding only in one direction or a structure having a ramp surface in the forward direction and a steeper stop surface in the other. Alternatively a follower movable towards the track surface as described can be arranged to require an operator action before further movement is possible. Also any track can have tactile structures where a change in resistance takes place, for example to alert the user at critical points in the process or to bias the follower into predetermined positions such as when aligned with a continuing track part. Optionally the tactile structure also provides an audible click confirmation. Grooves or ridges in the over the track or the abovesaid one way structures can be used for this purpose.

As used herein "track system" refers to the total arrangement of tracks and followers in the device. For purposes of description the track system will often be described as comprising different tracks, in turn being divided in sections and parts. Such categorization shall not be regarded as binding as a different terminology or categorization gives the same functional result. The track system may comprise a single "continuous" track, in the sense that it can be traversed by a single follower, where cooperation with the follower assists in various operational phases. Preferably the track system incorporates more than one continuous tracks cooperating with at least one follower each. The two or more tracks may then be arranged in "parallel", meaning that over at least part of their operational range they are arranged to allow the same movement of the piston rods, which may be used to increase guiding rigidity and precision or to allow a smaller or slimmer device with maintained rigidity and precision. A threaded track for example may have two or more parallel threads with followers. Preferably the track system incorporates at least two "serial" or "serially" arranged tracks, meaning that the tracks are arranged for guidance of the piston rod into different movements, either in true series or enabled by engagement/disengagement of follower, which may be uses for larger design freedom or to adapt the track and follower characteristics different for different operational phases, e.g. parallel tracks followed by a single additional serial track allowing utilization of the full circumference of the device. Another advantage is that serial tracks normally allows a more compact track system layout, e.g. less axial extension. Normally serial tracks requires the first follower to go out of engagement when the second follower goes into engagement with its track. The disengagement can be made by letting the first follower leaving its track entirely, i.e. by having an "open" termination, by going from a line to an area guidance as described, by allowing multiple line guidance alternatives for the first follower corresponding to all movement options for the second follower or by use of movable followers as described.

General control features of the tracks are to provide either a stop for a piston rod movement or a change of its allowed movement direction. A permanent stop at a predetermined location or distance can be provided by giving a track a "closed" termination, i.e. the follower has no further movement alternative than possibly to go back. Such a permanent stop may be used at the end of the operation cycle, for example when the ejections programmed for are completed. The follower may then be allowed to move in the opposite direction in the same track, for example to permit re-filling of the container or it may be prevented therefrom, e.g. by a one-way structure behind, for example to block a disposable device from further use. In most other situations a stop for a running piston movement is preferably not permanent but combined with new movement options for the piston rod. The stop is then, preferably provided by a track wall where the track changes direction, preferably at a sharp change and most often at a substantially right angle to the current track part, e.g. at "knee", giving the follower only one new movement alternative, or at a "branch", giving the follower at least two new movement alternatives, preferably so that a change in piston rod movement is needed before a new movement alternative can be reached.

Track directional changes may be combined and repeated. If for example multiple knees are combined a "staircase" track shape can be provided if each second movement is made in the same direction and a "meandering" track shape can be obtained if each second movement change is made in opposite directions. If some or all of the knees are replaced with branches a "grid" track shape is possible, allowing more than one movement option in each grid intersection, creating multiple combined alternatives. The multiple directional changes described can with preference be used in multiple dose systems, preferably so that the track provides several axial sections combined with intermediate transversal and preferably rotational movement sections, whereby the user experiences definite stop at the end of each dosing with the requirement for an active directional change. The axial sections can be of different lengths but it is preferred in most instances that the axial sections are of about equal lengths in each track to provide repeated equal doses, possibly with exception for the first axial part, which may be used to force the user making a de-aeration step of pre-determined volume and/or to initially discard content volume not to be used, and normally these volumes are different from the dosing volumes. Most preferably the equal axial parts represent an integer division of the whole container content and when several tracks are arranged for they may provide different integer divisions of the total volume. The transversal section can also be given varying length, e.g. larger than one track width, shorter than two track widths if the stop surface is sufficient, normally at least two widths but can be longer but preferably less than the available circumference. Space considerations may be determining but also e.g. positioning of readable scales or indicia, for which purpose small transversal movements may serve to keep axially arranged characters within trail of window limits and large transversal movements may serve to bring large characters out of a windows and new in. These considerations also apply for transversal movements in single dose applications.

While axial piston rod movements generally performs an active function on container content, rotational movements may be used for other purposes. One such purpose have been indicated above in multidose arrangements where rotational movements are used to assist in stopping one dose operation and requiring an active step before a new dose can be delivered. A further preferred purpose of a rotation track is to allow for selection between several axial tracks branching off from the rotational track, which then preferably may be designed in ring form, either at least partial ring form with closed termination to permit only reciprocating movements or preferably as a complete ring allowing full rotation of the follower therein. A third preferred use of a rotational track is to allow for a screw-threaded movement of the piston, rod performing both an axial and a rotational movement, which may be used for known purposes, e.g. change of speed or force ratio to eject small controlled volumes, high viscosity products or perform controlled reconstitution of multiple chamber containers, as known per se. The thread may extend only partially over a complete revolution, e.g. for ejection of small volumes, up to several turns, e.g. in reconstitution. It is fully possible to use threads of varying or pitch if the follower is designed accordingly, as indicated above. Generally rotation is made around a line concentric with the container axis.

A preferred use of ring track is as a joining track for several tracks branching of from the ring track and running at least partially in the axial direction. This layout can be used to provide for different track programs for differences in container type, container content type or patient requirements. Especially the layout is useful as a dose setting arrangement for a given container. The ring track should preferably provide for a line guidance of the follower, either by itself or in combination with a second track, as any uncontrolled axial movement of the piston rod may result in a dosing or initiation error or create uncertainty with the user. Dosing, or expelling, tracks branching off from the joining track and running at least partially in the axial direction, preferably for forward movement of the piston rod when moving from the joining track to the dosing tracks, may be of the general types outlined above, i.e. being arranged for single or multiple ejections. It is preferred that at least two, and preferably all, of the tracks are different, preferably by providing for different stroke lengths.

It is also preferred to arrange for readable dose indications in connection with dose selection arrangements. Generally the program provided forces the user into a single chain of sequential actions without alternatives but in connection with dose selection several alternatives are necessarily present and, although indications can be used in any phase, preferably indications are used for guidance in the dose selection phase. This can preferably be done so that indications or characters on one of the piston rod or housing parts are shown in a window, or pointed to by a pointer, on the other part. The characters may be positioned in a ring parallel to the joining track, e.g. on surfaces between the dosing tracks to conserve axial space or on a ring area free of dosing tracks, preferably to the rear of the dosing tracks, to enable use of larger characters.

It is also preferred to arrange for guided initiation steps in connection with this layout and in particular to provide for a controlled de-aeration step. As used herein de-aeration shall be regarded as including the possibility of pre-ejection of liquid, which in turn shall be understood to include discarding of liquid not to be used, which is an alternative known way of performing partial single dose ejections. De-aeration can be arranged for by providing each of the dosing tracks with an initial part, adapted in axial length for the de-aeration step, followed by a transversal part before the actual axial dosing part. Preferably the initial part for the different dosing tracks have about the same axial length, unless used for discarding, whereas the dosing part of the tracks preferably are different and preferably longer than the initial part. Another preferred layout, especially when discarding is not included in the de-aeration step, is to arrange an initiation track in the process before the joining track, so that the de-aeration takes place before the dose is selected, which gives a proper action sequence, necessitates only one initiation track for all dosing tracks and automatically gives the same initiation length for all the dosing tracks. The initiation track should run an axial distance suited for de-aeration and preferably land on a stop surface to require an active directional change for dose track selection. Preferably the stop is a wall of the joining track not allowing entrance to any dosing track, e.g. between such entrances. The initiation may include other process steps than the de-aeration and preferably then is preceded still earlier by a mixing track for multiple chamber containers. Such a track can be substantially axial, e.g. straight and terminated with a knee or branch, but is preferably screw-threaded as known per se, and may contain several parallel thread tracks with several followers as generally described above.

As indicated above a screw-threaded track, with constant or varying pitch, may be used for several purposes of which not all need any additional actions after the screw movement, for example when the movement is used for final ejection of small or high viscosity doses. In contrast, when used for multiple chamber reconstitution most process steps comes later in the cycle and it is desirable to provide a track system integrating these demands and in particular such a track system incorporating multiple dosing since multiple chamber systems frequently are designed to result in multiple doses after mixing, which hitherto has required complicated injector mechanisms. Hence a preferred track system layout incorporating screw-threaded tracks is to incorporate also a track for multiple dosing, e.g. any of the general types outlined above such as of staircase, meandering or grid type with only one or several selectable tracks. In order to enable this it is preferred to provide a joining track of the general ring type described above and let the threaded track continue directly into the joining track, which is possible with only a small directional change, the magnitude of which depends on the thread pitch. With the follower in the joining track all the optional alternatives described in relation the branching layout described above are available, especially for selection of several continuing tracks. Another preferred alternative is to let the thread track continue substantially in the axial direction, whereby the user will experience a stop for the threaded movement indicating that an axial movement is now necessary. The axial track part may be the entrance of a dosing track for single or preferably multiple doses as described. Preferably, however, the first part of the axial part is a de-aeration track, running a length adapted for this purpose, which may then continue in a knee or branch for single or multiple selection dosing tracks respectively, which dosing tracks in turn may be designed for single or multiple sequential dosing. The axial length of the de-aeration track is preferably different from the axial length of the dosing tracks, which in turn may be individually different but when of multiple dose type preferably each has repeater dosing sections of equal axial length. The arrangements described are fully compatible with two or more parallel tracks, having at least one follower each, e.g. by parallel threads continuing into parallel de-aeration tracks and parallel dosing tracks.

The above layouts have been described as if composed of continuous tracks in the sense that they can be traversed by a single follower. It is fully possible to modify the layouts to instead use two or more serial tracks as with corresponding advantages as generally described earlier. A preferred use of serial tracks is to use a first track with first follower, or preferably two or more parallel first tracks with first followers, for initial steps in the cycle, preferably mixing step and/or de-aeration step and most preferably both whereas a second track with a second follower for dose setting and actual ejection or ejections, the first and second tracks with respective followers being arranged as serial. The initial steps may not require selection among several track alternatives but instead may require parallel tracks and several followers of high rigidity and precision for the extended piston rod extended in the early phases. The dose selecting step instead may require substantial surface and full utilization of available circumference for the several tracks and possible information display to the user. Use of serial tracks solves this problem and in addition permits a compact track system layout. The followers may be arranged on the same part for both of the serial tracks, i.e. on either the housing or the piston rod, e.g. for simplest layout, or the first tracks may be arranged on one of the parts and the second track on the other part, e.g. to increase available surface for the track system and allowing for example tracks on axially overlapping parts. It is possible to perform disengagement of the first followers and engagement of the second follower or followers by a rotational movement, e.g. with exits and entrance respectively for example arranged in a bayonet type arrangement, but it is preferred that follower disengagement and engagement takes place by an axial relative movement between track and follower, especially so that the disengagement and engagement take place at rear and front parts respectively of the part having the track system. In other respects the first and second tracks can be of the general types earlier outlined, e.g. a straight or preferably threaded track for mixing, a straight axial track for de-aeration and a ring shaped joining track for dose selection, branching into several single or multiple ejection dosing tracks.

The above description has been made with reference both to structural and operational features, directly or indirectly, or follows from the descriptions made of structures, functions and objects. The invention shall be regarded to incorporate and embrace both the device and method aspects and characteristics described. The methodological aspects are not separately repeated. It should be pointed out, however, that all layouts described are compatible with the crucial step of securing de-aeration of the container before ejections are made, a step often neglected although important to positively guide during operation, especially self-administration. A method for securing this operational phase may include the steps of a) displacing the piston rod forwards in a movement having at least a component in the axial direction, performing hereunder de-aeration and/or pre-ejection of the container content, b) rotating the piston rod in a direction different from that of step a), and c) advancing the piston rod forwards in a movement having at least a component in the axial direction, performing hereunder ejection of container content. During the de-aeration step the user should preferably hold the device so as to secure flow of container content from below and upwards, preferably by pointing the container opening at least partly upwards. Any other method step as described may be added.

In other aspects the injector of the invention may be used conventionally or as described in prior art. Below a summary of preferred actions. If the container is not pre-assembled in the device housing the operator inserts the container and possibly connects it to attachments provided and assemble parts involved. If the container is a dual or multiple chamber device mixing operation may be undertaken before attachment to the device but is preferably made when attached as described. Unless a needle, infusion tube or other delivery unit is already in place the operator may mounts such a device on the container opening and possibly removes any needle shield present. The opening is pointed roughly upwards and the movable wall is moved forward to expel air and possibly eject a small preparation amount to assure proper function. Preferably the wall is moved forward by disclosed herein. If applicable a dose setting operation may take place by any of the methods described. If applicable the device is moved so as to perform a penetration movement to bring the needle into a target object, e.g. human or animal tissue or any other material or device. One or more ejections may now be performed by any of the means and methods outlined. Finally any penetrating device may be withdrawn from its target site.

SUMMARY OF DRAWINGS

FIGS. 1A to 1D show a preferred embodiment of the injector, FIG. 1A being a side transparent projection, FIG. 1B being an axial view of the housing rear part, FIG. 1C being a side view of the piston rod and FIG. 1D being a cross-section of the piston rod as indicated in FIG. 1C.

DESCRIPTION OF DRAWINGS

Figure 1D:
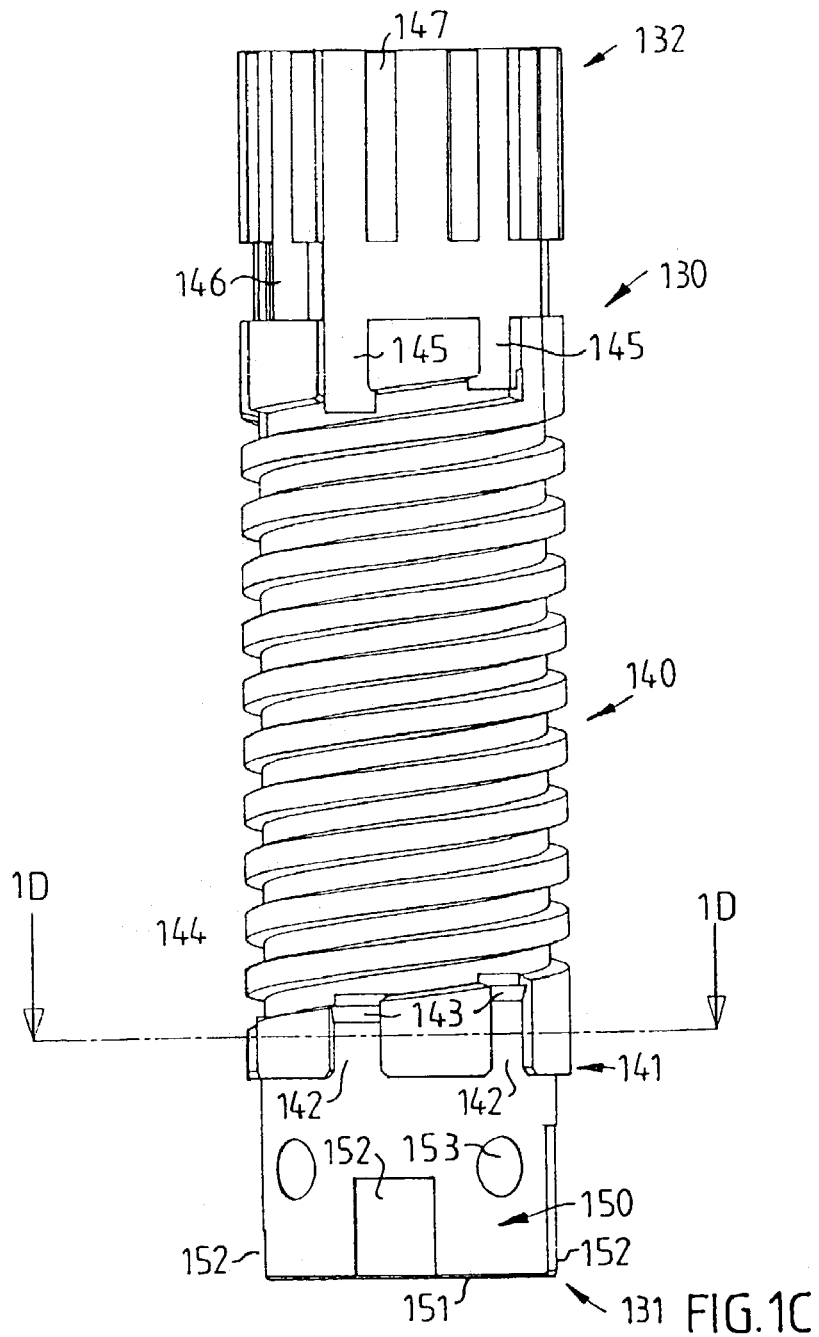
Figure 1D:
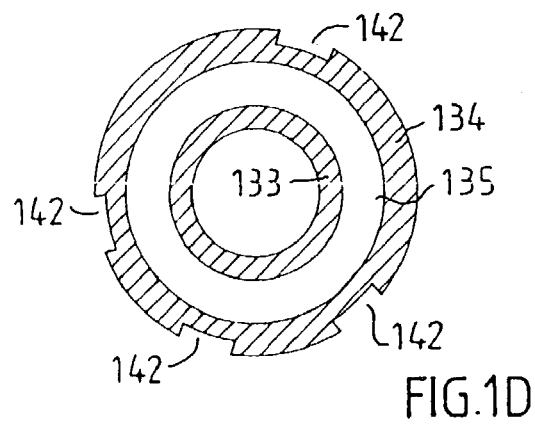

The embodiment of FIG. 1 is an injector having followers on the housing interior surface and a track system on the outer surface of an enlarged piston rod part in the form of a sleeve, extending from the piston rod rear end and forwards to be concentric with a penetrating part in its interior, which penetrating part abuts container movable wall. The injector is made for dual chamber containers of syringe type and its track system incorporates two parallel tracks having threaded and axial sections for two chamber mixing and de-aeration respectively and a further serially arranged track incorporating a ring shaped joining track and four branching axial dosing tracks for single dose ejection of any one of four different selectable volumes.

FIG. 1A illustrates the injector in an operational phase immediately after mixing of the two container chambers and immediately before a de-aeration step. The injector, generally designated 100, comprises a housing 110 composed of a lower integral part 111 and an upper integral part 112, joined by hooks 113, allowing separation for insertion and removal of the dual chamber container 120. The container 120 comprises a barrel 121, a front opening 122 with a neck and a membrane for needle piercing, a by-pass section 123 with inclined grooves for liquid overflow, a rear piston 124 and a front piston 125. Since the device is shown after chamber mixing, the front piston 125 has been moved into the by-pass section 123 and the rear piston 124 abuts the front piston after overflow of all liquid initially present between the pistons. Further forward movement of the pistons will be used for de-aeration and mixture ejection. The lower housing part has a narrowing front part, adapted to axially retain the container at the opening 122 neck. Rearward movement of the container is prevented by the penetrating part of the piston rod, which penetrating part is in abutment with the rear piston 124. The rear housing part 112 has a fingergrip 114 for ease of manipulation. It also carries the various followers. A first set of followers are arranged at the rearmost part of the upper housing part 112 where the housing has inwardly projecting structures 115 forming rear followers. Two more followers are hidden. On the inside at the front end of rear housing part 112 is arranged a single second follower 116 in the form of a rectangle, which in FIG. 1A is partially hidden behind the rear piston 124 and the bypass 123. This housing part also has a window 117, partially hidden, for exposure of dose values.

The followers are better seen in FIG. 1B, showing the upper housing part in view from rear. The four rear followers 115 at the housing rear end are asymmetrically arranged around the circumference and three of the followers are arranged to cooperate with one of the parallel tracks while the fourth is arranged to cooperate with the other parallel track, all asymmetry serving to secure that the piston rod part can be assembled with the housing only in one way. For good cooperation with the tracks in thread form the four rear followers are somewhat inclined and positioned at slightly different axial depths. The single front follower 116 is slightly larger and has a straight upper edge for cooperation with a circumferential edge of the piston rod.

Reference is made to FIG. 1C and 1D for piston rod details. The piston rod 130 has a front end 131 for insertion into the housing and a rear end 132 for gripping. As best seen in FIG. 1D the piston rod is composed of a penetrating part 133, designed for entrance into the container barrel interior and for abutting and displacing the rear piston 124, a sleeve 134 concentric with the penetrating part but running on the container outside, and arranged with the track system on its surface. Between the penetrating part 133 and the sleeve 134 is a spacing 135 adapted to accommodate the container barrel 121. Penetrating part 133 and sleeve are joined at the piston rod rear end 132. Describing first the parallel tracks 140 of the track system these tracks have an entrance 141 for the rear followers 115 axially located at the section for FIG. 1D, the entrance comprising four short entrance sections 142 located around the circumference so as to correspond to the four rear followers 115. At the rear end of each entrance section is a one-way structure 143, serving to facilitate insertion of the piston rod in the housing past the rear followers but to retain the piston rod thereafter. As said, three of the rear followers enter into one of the parallel tracks and one rear follower enters into the other parallel track. The entrance sections terminate in the respective threaded sections 144 of the parallel tracks, the length of which threaded sections are adapted for the mixing operation by displacement of the rear piston 124 a distance at least corresponding to the initial distance between rear piston 124 and front piston 125 plus displacement of the front piston into the by-pass section 123. The threaded sections terminate in axial de-aeration sections 145 which are four and have the same distribution as the entrance sections, allowing exit of the four rear followers 115 during an axially forward movement of the piston rod for the purpose of performing de-aeration. The positions and apparent length of the de-aeration sections are somewhat different due to the different axial location of the individual rear followers 115. The de-aeration tracks 145 terminate in a ring shaped disengagement track 146, which is axially wide enough to accommodate all of the axially differently located rear followers 115 with some tolerance, meaning that the earlier line guidance now is an area guidance both axially and transversely. During the axial movement into the disengagement track the serially arranged track part 150 comes into play. The serial track part comprises a circumferential edge 151, acting as a joining track for four dosing tracks 152, in the form of four slits of different length, branching form the joining track 151. The front follower 116 is positioned so that during the axial de-aeration movement, and under disengagement of the rear followers 115, the edge 151, at a point between and without dosing tracks, comes into abutment with the front follower 116 upper edge, thereby terminating the de-aeration step by stopping the axial movement and simultaneously engaging the front follower 116 with the joining track 151. The length of the de-aeration stroke is roughly indicated by arrow h in FIG. 1A. The piston rod may now be rotated with the front follower 116 engaged at edge 151 for selection of one of the dosing tracks 152 and during such rotation different dose values, printed on surfaces 153 and corresponding to each dosing track, are exposed in window 117. After selection of a dose the front follower is aligned with the corresponding slit or dosing track, enabling a forward movement of the piston rod to expel a dose, which axial movement is stopped at the closed termination of the dosing track. During the expulsion movement the rear followers 115 may enter between the gripping ribs 147 at the rear end 132, which ribs are sized and distributed so that the rear followers fits between them independent of which of the dosing tracks are used.

Figure 2A:
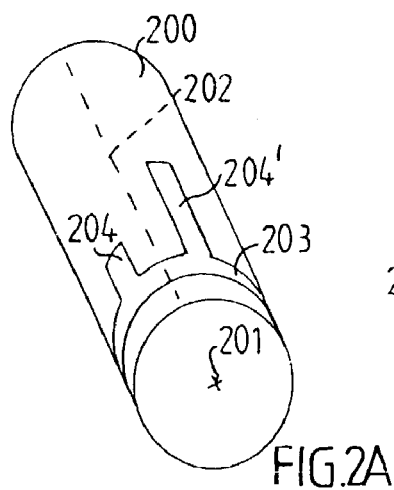
FIG. 2A illustrates a schematic form of a track system layout on a theoretical surface in cylindrical form.

FIG. 2A to 2F illustrates in schematic form some track system layouts on a theoretical surface. The surface, generally designated 200 can be either a surface on the piston rod or a surface on the housing, e.g. the outer surface of the piston rod or the inner surface of the housing. Although the track system is illustrated on a single surface it is within the scope of the invention that the track system incorporates tracks on both the piston rod and the housing surfaces. In FIG. 2A the surface is shown in cylinder form around a symmetry axis 201, which overall form is suitable for physical implementation on an injector surface. In FIGS. 2B to 2F the cylindrical surface of FIG. 2A is shown unrolled to a flat plane, e.g. after cutting along line 202.

In FIG. 2A, a simple track system is shown on surface 200, comprising a ring track 203 acting as a joining track for axial dosing tracks 204 and 204', branching off from the joining track 203.

Figure 2B:
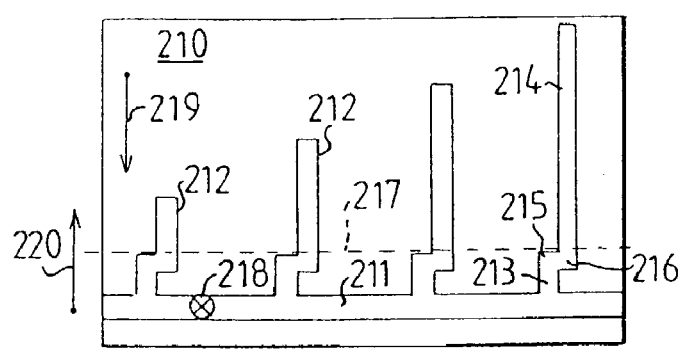
FIG. 2B illustrates a schematic form of a track system layout on a theoretical surface unfolded to a flat plane.

In FIG. 2B is illustrated a similar track system, comprising a ring track 211, acting as a joining track for four dosing tracks 212, branching off from the joining track. Each dosing track 212 comprises a first axial section 213, acting as a de-aeration track, and a second axial section 214, acting as an ejection track, which first and second sections are transversally displaced in relation to each other by being connected with a first knee 215 and a second knee 216. The axial length of the first section 213 of all dosing tracks 212 are the same, as illustrated by symmetry line 217, parallel with the joining track 211, whereas the axial length of the second axial sections 214 are different in order to enable ejection of different doses. A follower 218 is shown as a circle with a diameter adapted to the width of the tracks. In operation the follower 218 is able to move relative the surface 210 as determined by the tracks. The follower may first be moved around in ring track 211 for selection of a dosing track 212. Under movement in the first section 213 a de-aeration of the device container may take place until the movement is stopped at the first knee 215. The follower is then transversely displaced to reach the second axial section 214 for expulsion of content in an amount determined by the length of that section in the selected dosing track 212. If the plane 210 is placed on a piston rod surface and the follower 218 on a housing surface, the forward, expulsion, direction is downwards in the Figures, as illustrated by arrow 219 in FIG. 2B. If the plane 210 is placed on a housing surface and the follower 218 on a piston rod surface, the forward, expulsion, direction is upwards in the Figures, as illustrated by arrow in FIG. 2B. This applies to all of FIG. 2.

Figure 2C:
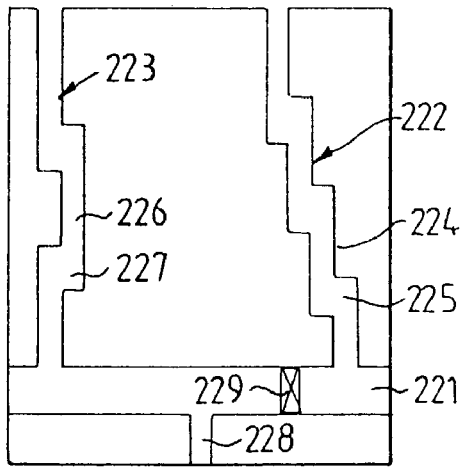
FIG. 2C illustrates a schematic form of another track system layout on a theoretical surface unfolded to a flat plane.

FIG. 2C illustrates a modified track system with multidose arrangements and another de-aeration arrangement. A joining track 221 branch into a stair multidose track 222 and a meandering multidose track 223. The stair multidose track 222 has repeated axial 224 and transversal 225 sections, where the transversal sections all run towards the left in the Figure, creating a staircase form of track 222, dividing the track into four consecutive dosing sections of about equal axial length. The meandering multidose track 223 also has repeated axial 226 and transversal 227 sections but the transversal sections runs interchangeably to the right and left in the Figure, creating a meandering form of the track 223, dividing the track into three consecutive dosing sections of about equal axial length. An initial de-aeration track 228 is arranged on the opposite side of joining track 221 from the multidose tracks and runs axially for a short distance adapted for de-aeration purposes. A follower 229 is here shown as an rectangle, illustrating that asymmetrical followers are possible to use if the tracks are configured accordingly, here with a corresponding larger width in the transversal parts than in the axial parts. In operation the follower 229 is moved relative the track system first to pass axially through the de-aeration track 228 until stopped against the opposite wall of joining channel 221. The follower is then moved transversally in the joining channel 221 for selection of either the stair multidose track 222 or the meandering multidose track 223. The follower is then moved axially to perform an expulsion until the axial movement is stopped at the knee in transversal section 225 or 227, again moved transversally to reach next axial section 224 or 226, which movement pattern is repeated for remaining doses.

Figure 2D:
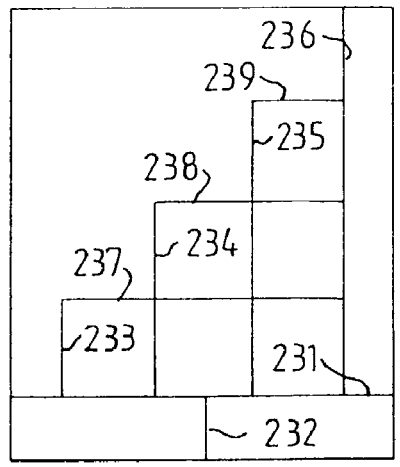
FIG. 2D illustrates a schematic form of yet another track system layout on a theoretical surface unfolded to a flat plane.

FIG. 2D illustrates a track system layout similar to that of FIG. 2C but modified with another multidose track layout. For illustration simplicity, in this and the following Figures, the tracks are shown as lines rather than channels with a width and can be thought of as the lines traversed by a point, rather than an area, on the follower. In FIG. 2D a joining track 231 is arranged with a preceding de-aeration track 232 as before. From the joining track 231 four dosing tracks 233, 234, 235 and 236 branch off axially. At the axial ends of tracks 233, 234 and 235 the tracks have a knee and continue transversally towards, and intersecting, the longer tracks, thereby creating new joining tracks 237, 238 and 239 from which said longer tracks branch off. If desired also these joining tracks can be extended into complete ring-tracks. The axial and transversal parts forms a grid track arrangement multiplying the operational possibilities. For example, in operation any of the four dosing tracks 233, 234, 235 and 236 can be selected when the follower is in the joining track 231 to expel e.g. ¼, ½, ¾ or all respectively of the total available volume and the user experiences a stop each selected dose. However, after using track 233 the option remains to expel still ¼, ½ or ¾ of the volume by selection of tracks 234, 235 and 236 respectively, still assisted with an end stop. After use of track 234 still ¼ or ½ of the volume can be ejected from tracks 235 and 236 and after use of track 235 still ¼ of the volume can be ejected form track 236.

Figure 2E:
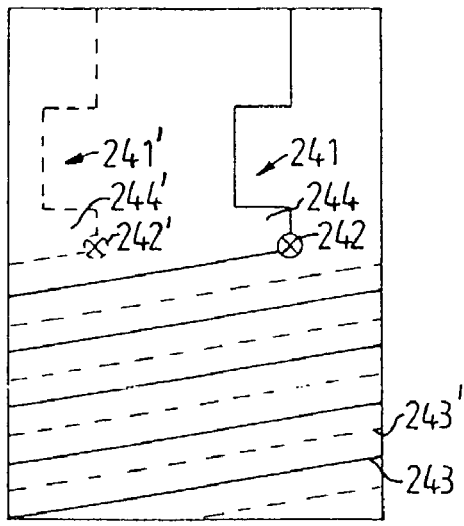
FIG. 2E illustrates a schematic form of still another track system layout on a theoretical surface unfolded to a flat plane.

FIG. 2E illustrates the use of parallel tracks, having threaded, axial and transversal sections. Two parallel tracks, generally designated 241 and 241' and shown in solid and dashed lines respectively, have one follower each, 242 and 242' respectively and the tracks and followers are arranged so that they can be engaged concurrently during passage of all shown track parts. The two tracks are continuous without branching, although branches can be added if desired. Each track has an initial threaded section 243 and 243', adapted for mixing of multiple chamber containers, continuing in a short axial section 244 and 244', adapted for de-aeration, and finally continuing in meandering multidose sections 245 and 245', adapted for repeated expulsion of a series of doses. In operation each follower 242 and 242' first passes through the threaded section 243 and 243' under rotation of the cylinder until this movement is stopped at the knees where the followers are shown in the Figure. An axial movement is now enabled for de-aeration in the axial sections 244 and 244' until this movement is stopped at the following knee, requiring a new rotation to reach the meandering multidose sections 245 and 245' for repeated ejection of doses as earlier described.

Figure 2F:
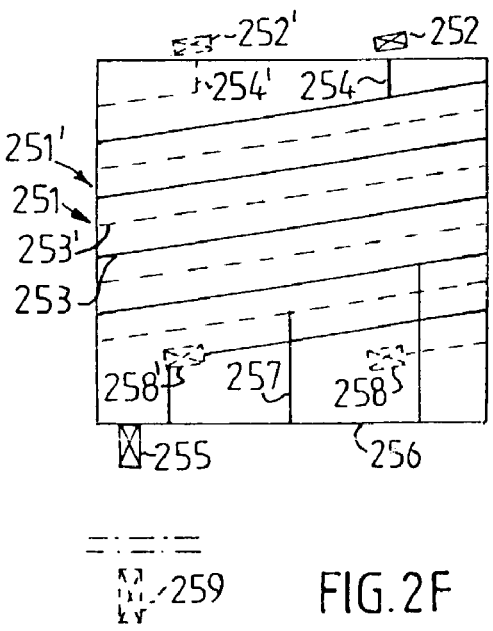
FIG. 2F illustrates a schematic form of a further track system layout on a theoretical surface unfolded to a flat plane.

FIG. 2F illustrates a modification with both parallel and serial tracks for single dose ejection. As in the previous embodiment there are two parallel tracks, generally designated 251 and 251', having one first follower each, 252 and 252' respectively. Each of the parallel tracks has initial threaded sections 253 and 253', continuing in short axial sections 254 and 254', adapted for de-aeration, from which the followers 252 and 252' may disengage by exiting from the axial sections 254 and 254' at the point where the followers are shown in the Figure. At this point in the sequence a second follower 255 reaches a ring shaped joining track 256 from which three dosing tracks 257 branch off. The second follower may now move under relative rotation of the parts until aligned with one selected dosing track 257 and perform an ejection when continuing axially in the selected dosing track. In phantom lines 258, 258' and 259 are shown the first and second followers in possible initial positions. It is clear that the second follower 255 with its joining track 256 and dosing tracks 257 forms a serial track layout, operable when the first followers 252 and 252' have been disengaged from their respective tracks. It is also clear that the track system can have a compact layout, partly due to overlapping parts, which do not interfere due to guidance by their respective followers, possibly assisted with followers of shape or dimensions compatible only with its own track as indicated in the Figure.

The invention is not limited to the embodiments described and illustrated but can be varied within the limits of the appended patent claims.

The invention claimed is:

1. Injector device for a syringe container, which syringe container comprises a barrel of axially substantially constant cross-section, a front opening and at least one container movable wall inserted in the barrel for displacement of a container content, the injector comprising a) a housing or housing part arranged to receive the container at least axially stationary, b) an integral or composite piston rod arrangement operable to displace the container movable wall at least in the forward direction, and c) a track system adapted to control or sequence the piston rod movements, the track system comprising at least one cooperating track and follower, the cooperating track and follower being arranged stationary with respect to the housing and the piston rod respectively, or vice versa, and in cooperation adapted to allow at least one forward movement of the piston rod, wherein the track system comprises a joining track running at least partly transversal to the axial direction, and at least two expelling tracks, each with a first end being connected to the joining track, adapted to allow the follower to selectively enter into any one of the expelling tracks, each expelling track running at least partly in the axial direction and in cooperation with the follower adapted to allow forward movement of the piston rod, and wherein each of at least two of the expelling tracks continues toward its second end in a first axial section, a knee or branch, and a second axial section transversely offset from the first axial section.

2. The injector of claim 1, wherein the at least two expelling tracks are different.

3. The injector of claim 1, wherein the joining track is arranged to give a line guidance in cooperation with the follower.

4. The injector of claim 1, wherein at least one of the expelling tracks comprises a stop surface for the follower, limiting the piston rod forward movement.

5. The injector of claim 4, wherein the at least two expelling racks have stop surfaces at different axial positions, providing piston rod limitations corresponding to different doses.

6. The injector of claim 4, wherein the stop surface is arranged to allow in cooperation with the follower no further transversal or forward axial movement of the piston rod.

7. The injector of claim 4, wherein the stop surface is arranged at a track knee or branch, allowing in cooperation with the follower a further transversal movement of the piston rod.

8. The injector of claim 7, wherein the track knee or branch is connected to at least one further track knee or branch, the further track knee or branch allowing in cooperation with the follower a further forward axial movement of the piston rod.

9. The injector of claim 1, wherein at least one expelling track continues into a second knee or branch and a third axial section, optionally further repeated.

10. The injector of claim 9, wherein the at least one expelling track is of a form selected from the group consisting of a staircase form, a meandering form, a grid form and combinations thereof.

11. The injector of claim 1, wherein the first axial section of each of the at least two expelling tracks have the same axial length, adapted for an initiation step.

12. The injector of claim 1, wherein the track system comprises an initial track, with one end being connected to the joining track, allowing the follower to enter from the initial track into the joining track under forward movement of the piston rod.

13. The injector of claim 12, wherein the initial track is connected to the joining track at a point where further axial movement is prevented by a wall surface of the joining track.

14. The injector of claim 12, wherein the initial track has a track section allowing forward movement of the piston rod over a predetermined axial length adapted for de-aeration of the container.

15. The injector of claim 12, wherein the initial track has a section allowing forward movement of the piston rod over a predetermined axial length.

16. The injector of claim 15, wherein the predetermined axial length is adapted for mixing of a dual or multiple chamber container.

17. The injector of claim 15, wherein the section comprises a screw-threaded track.

18. The injector of claim 17, wherein the screw-threaded track comprises at least two parallel threaded tracks with at least one follower each.

19. The injector of claim 1, wherein one or several one-way structures are arranged in the track system to prevent movement in one direction.

20. The injector of claim 19, wherein the one-way structure is arranged for manual control.

21. The injector of claim 1, wherein one or several friction altering structures are arranged in the track system.

22. The injector of claim 1, wherein more than one follower is used for different parts of the track system.

23. The injector of claim 22, wherein the different parts are serially arranged.

24. The injector of claim 22, wherein the different parts are arranged in parallel.

25. The injector of claim 1, wherein displayed information and an information selector are arranged on the housing part and the piston rod part, respectively, or vice versa.

26. The injector of claim 25, wherein the selector incorporates one of a window or a pointer.

27. The injector of claim 25, wherein the information is displayed on the housing part or piston rod part carrying the track system.

28. The injector of claim 25, wherein the information is displayed in relation to each expelling track.

29. The injector of claim 25, wherein the information is displayed in the form of a ring concentric with the container axis.

30. The injector of claim 29, wherein the ring is arranged on the piston rod.

31. The injector of claim 30, wherein the information is displayed between expelling tracks.

32. The injector of claim 29, wherein the information is displayed axially separate from the expelling tracks.

33. An injectable syringe device, comprising
  (a) a container including a barrel of axially substantially constant cross-section, a front opening and at least one container movable wall inserted in the barrel for displacement of a container content, and
  (b) the injector device of claim 1.

* * * * *